US012678627B1

(12) United States Patent
Adamson et al.

(10) Patent No.: US 12,678,627 B1
(45) Date of Patent: Jul. 14, 2026

(54) SYSTEMS AND METHODS FOR CLOSED-LOOP OR PARTIALLY CLOSED-LOOP BAROREFLEX ACTIVATION THERAPY

(71) Applicant: CVRx, Inc., Minneapolis, MN (US)

(72) Inventors: Philip B. Adamson, Austin, TX (US); Seth J. Wilks, Valparaiso, IN (US); Paul Pignato, Jacksonville, FL (US); Tucker Stuart, North Saint Paul, MN (US); Bart Carey, Maplewood, MN (US)

(73) Assignee: CVRx, Inc., Minneapolis, MN (US)

( * ) Notice: Subject to any disclaimer, the term of this patent is extended or adjusted under 35 U.S.C. 154(b) by 0 days.

(21) Appl. No.: 19/347,206

(22) Filed: Oct. 1, 2025

Related U.S. Application Data

(60) Provisional application No. 63/795,955, filed on Apr. 28, 2025.

(51) Int. Cl.
*A61N 1/36* (2006.01)
*A61N 1/02* (2006.01)
(Continued)

(52) U.S. Cl.
CPC ......... *A61N 1/36139* (2013.01); *A61N 1/025* (2013.01); *A61N 1/36114* (2013.01);
(Continued)

(58) Field of Classification Search
CPC ............... A61N 1/36139; A61N 1/025; A61N 1/36114; A61N 1/36132; A61N 1/36142; A61N 1/37282
See application file for complete search history.

(56) References Cited

U.S. PATENT DOCUMENTS 7,499,747 B2    3/2009  Kieval et al.
7,643,875 B2    1/2010  Heil et al.
(Continued)

FOREIGN PATENT DOCUMENTS

WO    2007136851    11/2007
WO    2011146393    11/2011

*Primary Examiner* — Brian T Gedeon
(74) *Attorney, Agent, or Firm* — Pauly, DeVries Smith & Deffner LLC

(57) ABSTRACT

Systems and methods are provided for delivering closed-loop or partially closed-loop baroreflex activation therapy (BAT) to treat conditions associated with autonomic dysfunction. A pulse generator delivers stimulation while physiological data, such as ECG, heart rate variability, bioimpedance, and physical activity levels, is collected from one or more sensors. The data is analyzed to assess autonomic nervous system activity, and stimulation parameters are dynamically adjusted in response. In some embodiments, adjustments are made on a beat-to-beat basis using ECG input. Artificial intelligence algorithms may be used to predict patient-specific responses, optimize therapy, and evaluate effectiveness. The method may further include integrating patient-reported symptoms, wirelessly transmitting data, or adjusting stimulation duty cycle based on time of day. The system may further incorporate patient-reported symptoms, a clinician dashboard for remote monitoring, and a multi-channel lead. Stimulation may be delivered non-invasively or via an implantable device.

20 Claims, 9 Drawing Sheets

(51) Int. Cl.
 *A61N 1/372* (2006.01)
 *G16H 40/67* (2018.01)

(52) U.S. Cl.
 CPC ..... *A61N 1/36132* (2013.01); *A61N 1/36142*
 (2013.01); *A61N 1/37282* (2013.01); *G16H*
 *40/67* (2018.01)

(56) References Cited

U.S. PATENT DOCUMENTS

| | | | |
|---|---|---|---|
| 8,000,793 B2 | 8/2011 | Libbus | |
| 8,195,289 B2 | 6/2012 | Heil et al. | |
| 8,442,640 B2 | 5/2013 | Libbus | |
| 8,606,359 B2 | 12/2013 | Rossing et al. | |
| 8,626,301 B2 | 1/2014 | Libbus | |
| 8,712,531 B2 | 4/2014 | Kieval et al. | |
| 8,818,513 B2 | 8/2014 | Libbus | |
| 12,257,434 B2 | 3/2025 | Georgakopoulos et al. | |
| 2005/0149132 A1 | 7/2005 | Libbus | |
| 2005/0288728 A1* | 12/2005 | Libbus | A61N 1/3614 |
| | | | 607/42 |
| 2006/0253161 A1* | 11/2006 | Libbus | A61N 1/36139 |
| | | | 607/18 |
| 2007/0021794 A1 | 1/2007 | Kieval et al. | |
| 2007/0021799 A1 | 1/2007 | Kieval et al. | |
| 2007/0038262 A1 | 2/2007 | Kieval et al. | |
| 2008/0009916 A1 | 1/2008 | Rossing et al. | |
| 2008/0009917 A1 | 1/2008 | Rossing et al. | |
| 2008/0027526 A1* | 1/2008 | Zarembo | A61N 1/0568 |
| | | | 607/120 |
| 2008/0058872 A1* | 3/2008 | Brockway | G16H 40/67 |
| | | | 607/2 |
| 2008/0288017 A1 | 11/2008 | Kieval et al. | |
| 2009/0076397 A1* | 3/2009 | Libbus | A61B 5/259 |
| | | | 600/509 |
| 2009/0132002 A1 | 5/2009 | Kieval | |
| 2009/0198294 A1 | 8/2009 | Rossing et al. | |
| 2010/0298898 A1 | 11/2010 | Libbus | |
| 2016/0045741 A1* | 2/2016 | Libbus | A61N 1/36057 |
| | | | 607/116 |
| 2020/0345240 A1* | 11/2020 | Aranda Hernandez | |
| | | | A61B 5/076 |
| 2020/0376280 A1* | 12/2020 | Shuros | A61N 1/36585 |
| 2024/0017068 A1* | 1/2024 | Pannu | A61N 1/36132 |

* cited by examiner

SYSTEMS AND METHODS FOR CLOSED-LOOP OR PARTIALLY CLOSED-LOOP BAROREFLEX ACTIVATION THERAPY

CLAIM OF PRIORITY

This non-provisional patent document claims the benefit of priority under 35 U.S.C. § 119(e) to U.S. Provisional Patent Application Ser. No. 63/795,955, entitled "SYSTEMS AND METHODS FOR CLOSED-LOOP OR PARTIALLY CLOSED-LOOP BAROREFLEX ACTIVATION THERAPY," filed on Apr. 28, 2025, which is incorporated herein by reference in its entirety.

TECHNICAL FIELD

This patent document relates to medical therapies and, more particularly, to systems and methods for influencing autonomic nervous system activity.

BACKGROUND

Baroreflex activation therapy (BAT) is a form of neuromodulation that involves stimulating baroreceptors to modulate autonomic nervous system activity. By activating baroreceptors, BAT reduces sympathetic nervous system activity while enhancing parasympathetic tone. BAT has been clinically validated for the treatment of heart failure.

Overview

Despite its clinical potential, conventional BAT systems rely on fixed stimulation protocols that do not dynamically adjust to patient-specific physiological changes, potentially limiting both therapeutic efficacy and safety. In addition, current BAT approaches operate in isolation, without integration into broader digital health ecosystems. This lack of coordination with other implantable or wearable devices represents a missed opportunity to optimize care. Limited interoperability with personal health technologies further prevents patients from accessing aggregated, meaningful data that could improve engagement, adherence, and self-management.

Moreover, existing BAT implementations do not take advantage of modern tools for optimizing stimulation. Therapy titration is often imprecise, reactive, and inconsistent. Patients and clinicians have limited insight into how treatment affects long-term health outcomes, and current systems rarely incorporate user feedback or behavior into therapy decision-making.

The present inventors have recognized several limitations in existing BAT systems, including a lack of personalization, dynamic adaptability, and meaningful integration with physiological signals and patient-reported feedback. To address these shortcomings, the inventors have developed novel systems and methods for delivering BAT in a closed-loop or partially closed-loop configuration that is responsive to real-time physiological signals and tailored to individual patient needs.

The disclosed methods include delivering electrical stimulation to one or more baroreceptors using a pulse generator, collecting physiological data from wearable, implantable, or external sensors, analyzing the data to assess autonomic nervous system activity, and dynamically adjusting stimulation parameters, such as amplitude, pulse width, frequency, and duty cycle, in response. In certain embodiments, adjustments occur on a beat-to-beat basis using electrocardiography (ECG) inputs. Artificial intelligence algorithms may be applied to refine stimulation based on real-time and historical data, predict patient-specific responses, or assess therapy effectiveness.

Additional features include detection of early signs of heart failure decompensation, integration of patient-reported symptoms via a patient interface, and wireless data transmission to a clinician dashboard for remote monitoring and therapy optimization. The system may further include multi-channel leads, implantable or non-invasive devices, and tailored stimulation synchronized with the cardiac cycle.

Collectively, these systems and methods provide a scalable, intelligent, and patient-centered platform for treating a wide range of conditions associated with autonomic dysfunction.

These and other examples and features of the disclosed systems and methods will be described in greater detail in the following Detailed Description. This Overview is intended to present non-limiting examples of the disclosed subject matter and is not meant to serve as an exhaustive or exclusive explanation. Instead, the Detailed Description below provides further information regarding the design, implementation, and applications of the disclosed systems and methods.

BRIEF DESCRIPTION OF THE DRAWINGS

In the drawings, like numerals are used to describe similar features and components throughout several views. The drawings illustrate generally, by way of example, but not by way of limitation, various system and method embodiments discussed in this patent document.

Figure 1:
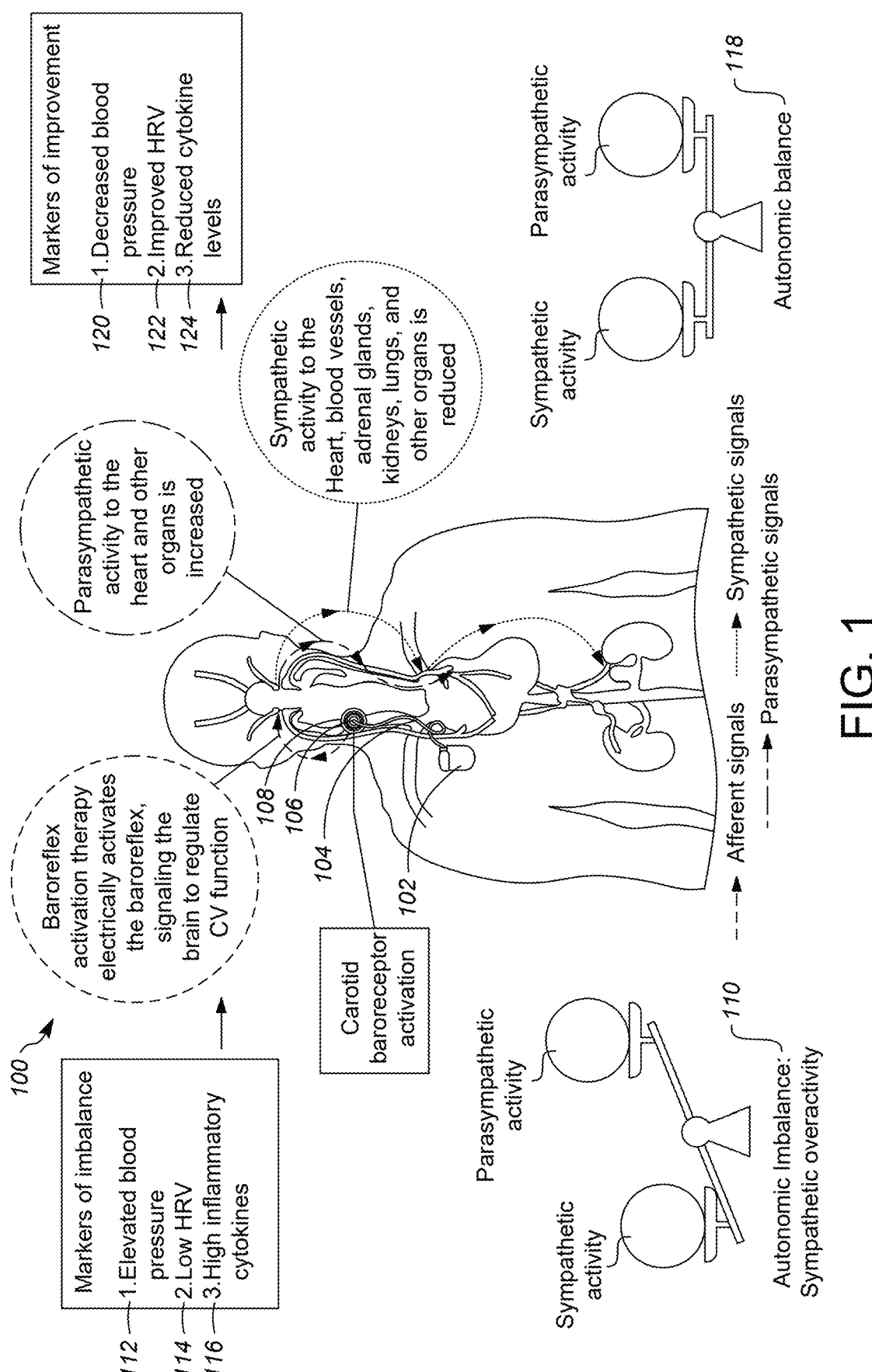
FIG. 1 is a schematic diagram illustrating the physiological impact of BAT, showing a transition from autonomic imbalance to restored equilibrium with improved physiological markers, as constructed in accordance with at least one embodiment.

The drawings are not necessarily to scale. Certain features and components may be shown exaggerated in scale or in schematic form, and some details may not be shown in the interest of clarity and conciseness.

DETAILED DESCRIPTION

The present disclosure relates to systems and methods for delivering closed-loop and partially closed-loop BAT for the treatment of conditions associated with autonomic nervous system dysfunction. Such conditions may include, but are not limited to, resistant hypertension, heart failure, inflammatory and autoimmune disorders, metabolic syndromes, chronic pain, and arrhythmias. The disclosed techniques enable real-time or near-real-time modulation of baroreceptor activity using electrical stimulation dynamically adjusted in response to physiological and patient-reported data.

In exemplary embodiments, a pulse generator delivers electrical stimulation to one or more baroreceptors. Physiological data, such as ECG, heart rate variability, bioimpedance, inflammatory cytokine levels, and physical activity, is collected by wearable, implantable, or external sensors and analyzed to assess autonomic nervous system activity. Stimulation parameters, including duty cycle, pulse amplitude, frequency, and pulse width, may be automatically adjusted based on this analysis. In certain configurations, adjustments are made on a beat-to-beat basis using ECG data as input to synchronize stimulation with the cardiac cycle.

The system architecture can include a sensor suite, signal processing controller, and a patient engagement platform. Artificial intelligence algorithms may be employed to refine stimulation parameters based on historical and real-time inputs, predict therapeutic response, and identify early signs of decompensation, such as through correlation of ECG variability with acoustic and accelerometer data. The system may wirelessly transmit data to a clinician dashboard for remote monitoring and enable patient feedback through a digital interface. This platform supports personalized therapy optimization and scalable deployment across a wide range of clinical settings.

Pathophysiological Basis for BAT

Closed-loop or partially closed-loop BAT is designed to restore autonomic balance in patients with chronic conditions characterized by sustained sympathetic overactivity and insufficient parasympathetic compensation. The autonomic nervous system regulates critical physiological functions, including cardiovascular tone, metabolic processes, inflammatory signaling, and pain modulation. In many chronic diseases, this balance is disrupted, resulting in systemic dysregulation that manifests as elevated blood pressure, low heart rate variability (HRV), increased inflammatory cytokine production, and reduced metabolic resilience.

Conditions commonly associated with autonomic dysregulation include resistant hypertension, heart failure with reduced ejection fraction (HFrEF), autoimmune diseases such as rheumatoid arthritis and systemic lupus erythematosus, metabolic disorders like type 2 diabetes and obesity, and chronic pain syndromes such as fibromyalgia and neuropathic pain. In these conditions, an overactive sympathetic response contributes to disease progression and persistent symptoms. Patients frequently exhibit objective physiological markers of imbalance, including elevated resting heart rate, suppressed HRV, high levels of circulating stress hormones (e.g., cortisol), and elevated pro-inflammatory cytokines such as tumor necrosis factor-alpha (TNF-$\alpha$) and interleukin-6 (IL-6).

BAT works by electrically stimulating baroreceptors, mechanosensitive nerve endings primarily located in the carotid sinus. These baroreceptors send afferent signals to the central autonomic network, which reduces sympathetic outflow and enhances parasympathetic activity, promoting homeostasis across multiple systems. Unlike conventional neuromodulation approaches that deliver fixed or clinician-adjusted stimulation, closed-loop or partially closed-loop BAT dynamically adjusts therapy based on real-time physiological signals. This results in personalized, adaptive therapy finely tuned to the patient's evolving autonomic state.

As depicted in FIG. 1, a patient may be equipped with a baroreflex stimulation system (100) that includes an implantable pulse generator (PG) (102) and a lead (104) having one or more electrodes (106) positioned near the carotid sinus (108). In the untreated state (left side of the diagram), autonomic imbalance (110) is illustrated, characterized by increased sympathetic dominance and associated downstream effects, such as high blood pressure (112), low HRV (114), and elevated cytokine levels (116). Following BAT activation (right side of the diagram), the system (100) restores autonomic equilibrium (118), resulting in improvements in hemodynamic and inflammatory markers, including decreased blood pressure (120), improved HRV (122), and reduced cytokine levels (124). This visualization underscores the clinical rationale for the present systems (100) and methods and links BAT therapy to measurable pathophysiological phenomena observed across autonomic disorders.

PG and Lead Placement

Figures 2A, 2B, 2C:
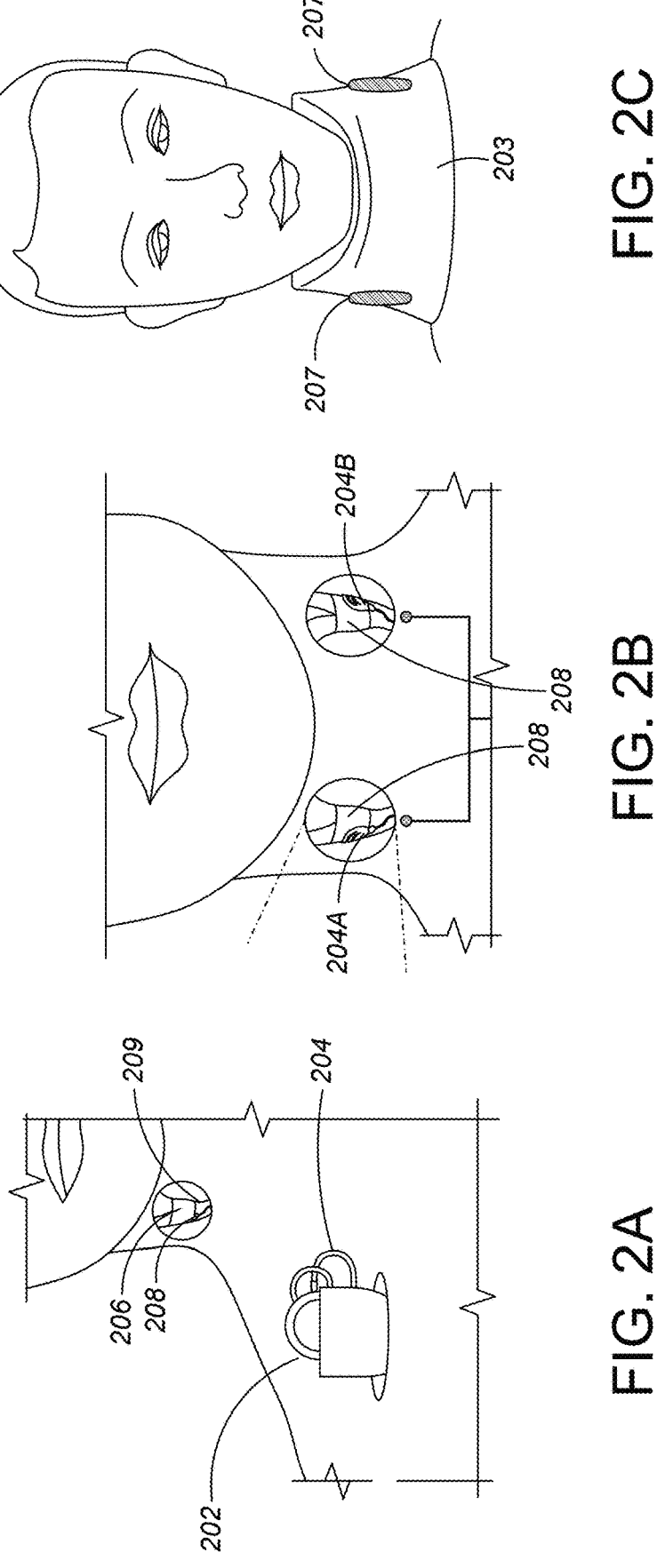
FIGS. 2A-C illustrate alternative configurations of the BAT system, including implantable and non-invasive options, as constructed in accordance with at least one embodiment.

As illustrated in FIGS. 2A-2C, the present disclosure provides both implantable and non-invasive configurations for PG and electrode placement to support BAT across a variety of clinical applications. FIG. 2A presents a schematic concept of an implantable system, shown as a cutaway diagram of the human chest. In this embodiment, the PG (202) is located subcutaneously in the infraclavicular region. A stimulation lead (204) is tunneled superiorly toward the neck, terminating in one or more electrodes (206) positioned adjacent to the carotid sinus (208), which is a baroreceptor activation zone. This vascular bifurcation of the common carotid artery (209) is densely innervated with baroreceptors that respond to changes in arterial pressure. Electrodes (206) are placed along the adventitial surface of the carotid artery (209) to ensure stable activation of baroreceptor afferent fibers while preserving the structural integrity of the vessel. In some embodiments, multi-channel electrode arrays are employed to allow either broad-field stimulation or targeted activation of discrete nerve regions. These arrays may be deployed unilaterally or bilaterally, depending on the patient's anatomy and therapeutic needs.

FIG. 2B illustrates a bilateral lead configuration, in which stimulation leads (204A, 204B) extend to both carotid sinuses (208). This configuration may provide enhanced modulation of autonomic tone, such as for severe/refractory conditions, reflecting the potential advantages of bilateral engagement in patients with advanced or treatment-resistant autonomic imbalance. The ability to stimulate both carotid sinuses (208) in a coordinated manner may offer improved modulation of autonomic tone and greater therapeutic efficacy.

In alternative embodiments, non-invasive stimulation systems are also contemplated. FIG. 2C depicts a wearable system, such as a neckband (203) or adhesive patch, positioned externally on the neck with surface electrodes (207) aligned over the carotid sinus. Placement may be guided by anatomical landmarks, including the sternocleidomastoid muscle and the angle of the jaw, to ensure appropriate alignment with the underlying baroreceptor field. Surface electrodes (207) can be operatively connected to the wearable controller, which delivers transcutaneous electrical stimulation to activate the baroreflex without requiring surgical implantation.

Both implantable and non-invasive configurations may incorporate positional sensors or closed-loop feedback mechanisms to optimize electrode placement, stimulation parameters, and ensure consistent engagement with the baroreceptor region. This design versatility supports a range of clinical uses, including long-term therapeutic application, short-term diagnostic evaluation, therapy titration, or patient screening.

Role of Closed-Loop or Partially Closed-Loop BAT in Treatment

The closed-loop or partially closed-loop BAT system is designed to deliver targeted electrical stimulation to baroreceptors in a manner that dynamically adjusts to the patient's physiological state. At the core of the system is a PG, which may be connected to a flexible lead with one or more electrodes positioned adjacent to the carotid sinus. This vascular region is densely populated with baroreceptors that serve as critical sensors of arterial pressure and regulators of autonomic output to the cardiovascular, metabolic, and immune systems.

Electrical stimulation of the carotid sinus activates the baroreflex arc, sending afferent signals to the brainstem that reduce sympathetic activity and increase parasympathetic tone. These neural effects can result in measurable physiological improvements, including lowered blood pressure, increased HRV, and reduced systemic inflammation. Such responses are particularly valuable in treating conditions like resistant hypertension, heart failure, metabolic disorders, autoimmune diseases, and inflammatory syndromes.

In alternative embodiments, the system may use non-invasive configurations in which adhesive surface electrodes are externally positioned over the neck to deliver transcutaneous stimulation aligned with the carotid sinus, for example. These non-invasive approaches are well-suited for short-term use, such as diagnostic evaluation, patient selection, or temporary therapy for patients unable to undergo surgical implantation. In some scenarios, hybrid systems combining implantable and external components may be deployed to meet specific clinical requirements.

What distinguishes the closed-loop or partially closed-loop BAT system from existing neuromodulation therapies is its integration with real-time or near-real-time physiological feedback. The system receives continuous input from a network of sensors strategically positioned throughout the body to monitor a range of biometric signals. These sensors may include a wrist-worn smartwatch for tracking heart rate and physical activity, a chest-mounted ECG patch for detailed cardiac rhythm analysis, and abdominal sensors for monitoring electromyography (EMG) signals and hydration status. Additional biosensors may also be employed to measure blood pressure, bioimpedance, and levels of circulating inflammatory biomarkers. This comprehensive physiological surveillance enables the system to adaptively modulate stimulation parameters in direct response to a patient's dynamic physiological state.

Collectively, these inputs provide a comprehensive and dynamic view of the patient's autonomic function.

The system uses this data to automatically adjust stimulation parameters, including amplitude, pulse width, frequency, and/or duty cycle, in real time. For example, when the system detects increased sympathetic activity or elevated blood pressure during exertion or psychological stress, it may increase stimulation intensity. During periods of rest or sleep, stimulation may be reduced or paused to conserve battery life and avoid overtreatment. This adaptive control mechanism allows the system to maintain autonomic homeostasis without requiring manual reprogramming.

Figure 3:
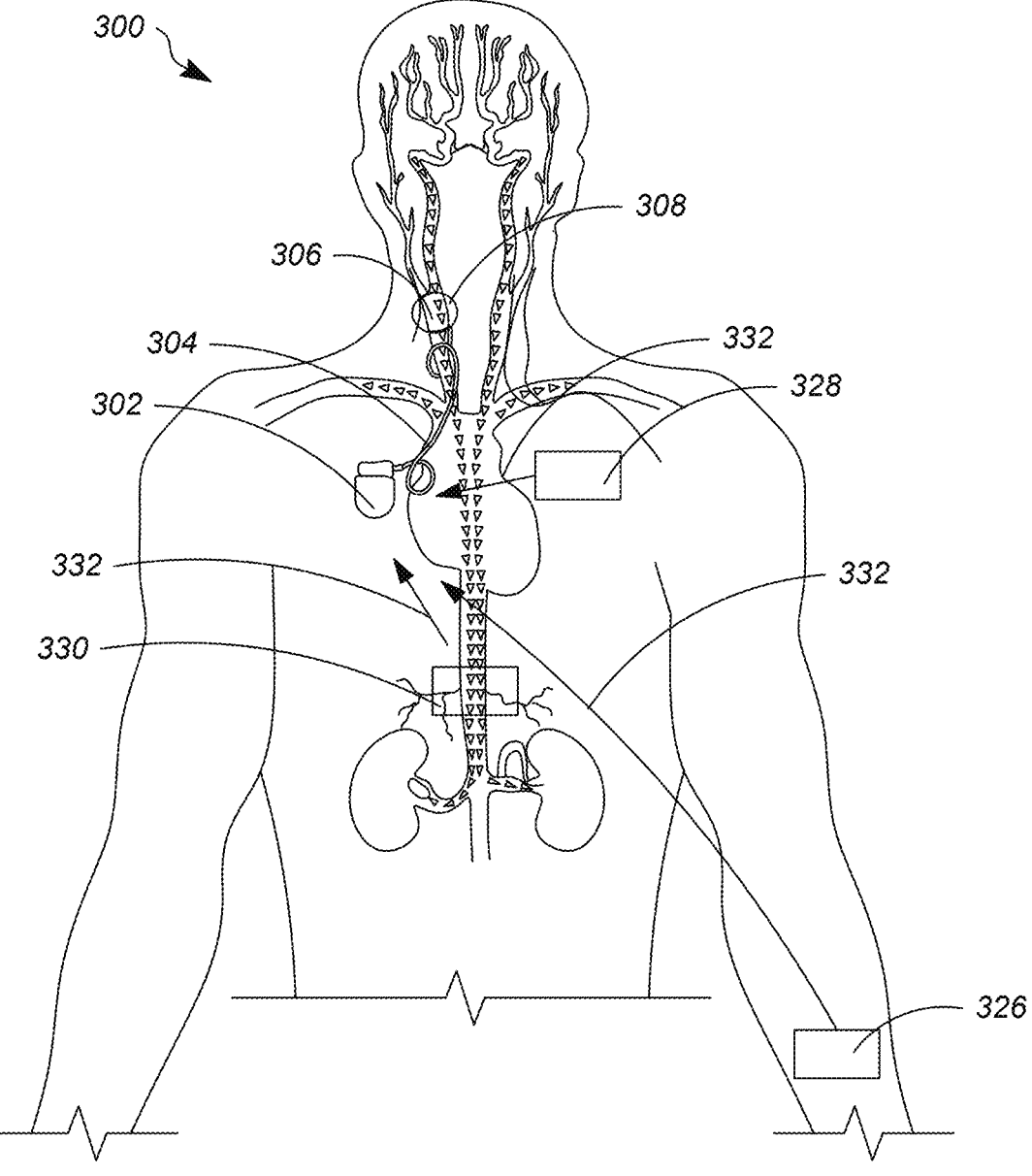
FIG. 3 is a diagram of a closed-loop or partially closed-loop BAT architecture, featuring an implantable pulse generator, distributed sensors, and adaptive stimulation modulation based on real-time physiological input, as constructed in accordance with at least one embodiment.

As illustrated in FIG. 3, the closed-loop or partially closed-loop BAT system (300) includes a dynamic feedback architecture that continuously adapts stimulation output based on real-time physiological input. The schematic concept highlights core system components, beginning with a PG (302) positioned subcutaneously near the clavicle. The PG (302) is connected to a stimulation lead (304) that extends toward the neck, terminating in one or more electrodes (306) placed adjacent to the carotid sinus (308). The system (300) further includes a network of distributed biosensors, represented graphically in the figure: a smartwatch (326) worn on the wrist can monitor heart rate and physical activity; an ECG patch (328) placed on the chest can capture detailed cardiac rhythm data; and abdominal sensors (330) can track EMG activity and hydration status. Additional biosensors may also be deployed to measure blood pressure, bioimpedance, and inflammatory biomarkers, for example, offering a comprehensive physiological view.

The feedback loop mechanism is visually depicted using directional arrows (332) that represent the continuous flow of data from the biosensors into the PG (302). These inputs enable the system (300) to make real-time adjustments to stimulation parameters, such as amplitude, pulse width, frequency, or duty cycle, based on the patient's current autonomic state. For instance, if sympathetic activity or blood pressure spikes during physical exertion or stress, the system (300) may automatically increase stimulation intensity. Conversely, during rest or sleep, it can reduce or pause stimulation to conserve battery life and prevent overtreatment. Through this adaptive mechanism, the BAT system (300) can maintain autonomic homeostasis without requiring manual intervention, offering a more responsive and patient-tailored therapeutic approach.

Signal Processing and Therapy Customization

The closed-loop or partially closed-loop BAT system includes a comprehensive suite of physiological sensors designed to continuously monitor patient status and support real-time therapeutic adjustments. This multimodal sensing architecture enables the system to assess autonomic function, inflammatory activity, hydration status, physical movement, and other parameters relevant to optimizing neuromodulation.

The system monitors a wide range of biosignals to assess and respond to the patient's physiological state, including HRV, bioimpedance, levels of inflammatory cytokines, muscle activity (EMG), hydration status, thermoregulation, stress response, and movement dynamics. To collect these data, the system incorporates various specialized sensors.

Chest-mounted ECG patches can provide detailed HRV and beat-to-beat cardiac analysis, while wrist-based photoplethysmography (PPG) sensors capture pulse waveform data. Hydration can be monitored using skin-adhered sensors or sweat patches. EMG sensors placed on the abdomen or limbs can detect physical exertion and compensatory gait patterns. Biomarker patches can be used to measure circulating pro-inflammatory cytokines, such as TNF-α and IL-6. Pupillometry sensors can assess sympathetic nervous system activity through changes in pupillary response, and temperature sensors can track thermal regulation. Additionally, accelerometers and gyroscopes can measure posture, movement, and activity levels across the day, providing a comprehensive picture of patient behavior and physiological status.

Data from these diverse sources can be processed using advanced signal processing methods. For example, beat-to-beat ECG analysis reveals fine-scale autonomic fluctuations, while acoustic signals captured by accelerometers may provide information on heart or lung sounds, relevant in monitoring heart failure status. Radiofrequency (RF) fluid characterization can assess tissue hydration or detect fluid shifts based on impedance and dielectric changes. These analytic techniques enable precise interpretation of complex and noisy physiological data.

To derive actionable insights from the continuous data stream, the system can incorporate artificial intelligence (AI) and machine learning (ML) algorithms. These models are trained to detect both acute deviations and long-term trends. For instance, the system may recognize a steady decline in HRV, a cytokine spike suggestive of inflammation, or changes in motion patterns indicating fatigue, instability, or decompensation. Upon detecting such events, the system can proactively adjust stimulation before overt symptoms manifest.

Stimulation parameters, including amplitude, frequency, pulse width, and/or duty cycle, can be dynamically customized based on the analyzed data. For example, during periods of heightened inflammation, the system may increase amplitude or frequency to suppress sympathetic activity. During sleep, stimulation frequency or duty cycle may be reduced to conserve energy and maintain circadian alignment. This adaptive approach supports continuous, patient-specific therapy across a variety of clinical conditions and use cases.

Figure 4:
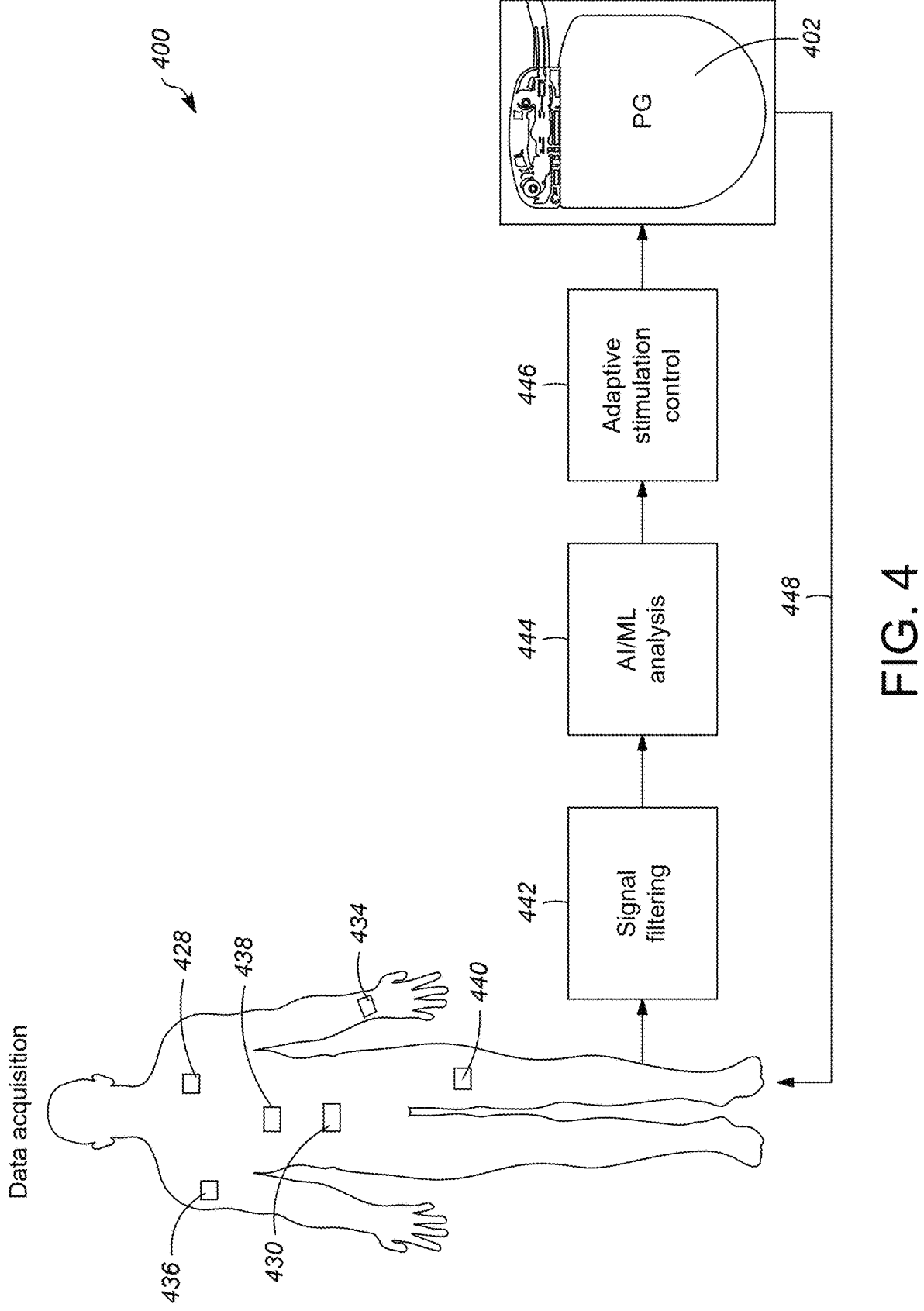
FIG. 4 represents the system's signal processing and therapy customization flow, including sensor placement, data analysis, and dynamic therapy adjustments informed by physiological trends, as constructed in accordance with at least one embodiment.

As illustrated in FIG. 4, the closed-loop or partially closed-loop BAT system (400) integrates a wide array of physiological sensors and advanced analytics to support intelligent, personalized therapy adjustments. A schematic concept for signal processing and therapy customization is shown through a labeled anatomical outline of the human body, highlighting the placement of key biosensors. These can include an ECG sensor (428) on the chest for HRV and beat-to-beat cardiac monitoring, a PPG sensor (434) on the wrist to capture pulse waveform data and physical activity, a hydration sensor (436) on the arm to assess fluid status, and an EMG sensor (430) on the abdomen to detect muscle activation and exertion. Additional components can include an accelerometer (438) on the torso for posture and movement analysis, and a skin-mounted inflammatory biomarker patch (440) for tracking cytokines such as TNF-α and IL-6.

Complementing this body diagram is a data flow schematic, which illustrates an example of the system's (400) signal processing sequence. Inputs from the distributed sensors are first subjected to signal filtering (442) to reduce noise and improve signal fidelity. The filtered signals are then processed by embedded AI and ML algorithms (444), which analyze both acute and longitudinal patterns in the data. These insights are translated into real-time stimulation adjustments (446)—illustrated by directional arrows indicating the flow from sensor input→signal filtering→AI/ML analysis→adaptive stimulation control—which are received by the PG (402). Specific control parameters may include amplitude, frequency, and pulse width adjustments, as well as duty cycle optimization to align with circadian rhythms and other physiological patterns. A continuous data flow from the PG (402) back to the biosensors can complete the closed-loop cycle (448).

Loop Control and Adaptive Feedback

The closed-loop BAT system operates using an adaptive feedback control architecture that continuously monitors physiological signals and dynamically adjusts stimulation parameters in real time. This closed-loop design enables the system to respond immediately to fluctuations in the patient's condition, such as elevated blood pressure, increased sympathetic tone, physical exertion, or psychological stress, ensuring consistent therapeutic benefit. By grounding stimulation adjustments in real-time physiological data, the system delivers highly responsive, individualized therapy.

In some embodiments, the system begins operation in a partially closed-loop configuration, referred to as the learning phase. During this phase, the device delivers static or semi-standardized stimulation while collecting continuous physiological and behavioral data. This information is used to generate a personalized treatment profile, including baseline autonomic activity, circadian rhythms, and early markers of responsiveness to stimulation. Once sufficient data is accumulated, the system transitions to a fully adaptive control mode, in which stimulation parameters are autonomously modulated in response to real-time deviations from baseline patterns.

The adaptive feedback loop integrates data from multiple sensor domains to inform stimulation decisions. Key autonomic indicators may include HRV, ECG waveform characteristics, and bioimpedance, which reflect cardiac and vascular tone. Behavioral and contextual inputs, such as movement patterns, posture changes, sleep quality, and patient-reported symptoms, provide further insight into the patient's physiological and emotional status. In some implementations, environmental factors like ambient temperature, time of day, or physical workload may also be used to further tailor therapy delivery.

Stimulation parameters, including pulse amplitude, pulse frequency, pulse width, and/or duty cycle, can be adjusted dynamically to maintain efficacy while avoiding overstimulation. For instance, during periods of rest or sleep, the system may reduce the duty cycle to promote recovery and conserve battery life. Conversely, during stress or physical exertion, it may temporarily increase amplitude or frequency to counterbalance heightened sympathetic activity. These adjustments are made automatically based on incoming data, without requiring manual intervention from a clinician.

This intelligent feedback-driven system minimizes the need for routine reprogramming and facilitates long-term personalization of therapy. By aligning stimulation output with the patient's evolving physiological and behavioral state, the system enhances therapeutic consistency, improves patient comfort, and supports sustained clinical outcomes over time.

The control architecture forms a continuous adaptive feedback loop. The diagram depicts the flow of multimodal sensor input, such as HRV, EMG, and hydration levels, into the system. These signals are processed and compared against a personalized physiological baseline to detect deviations from the patient's normal state. Based on these deviations, the system automatically adjusts stimulation parameters in real time to maintain therapeutic effectiveness. This process is followed by ongoing physiological monitoring, completing the feedback cycle and enabling continuous, responsive therapy delivery.

Figure 5:
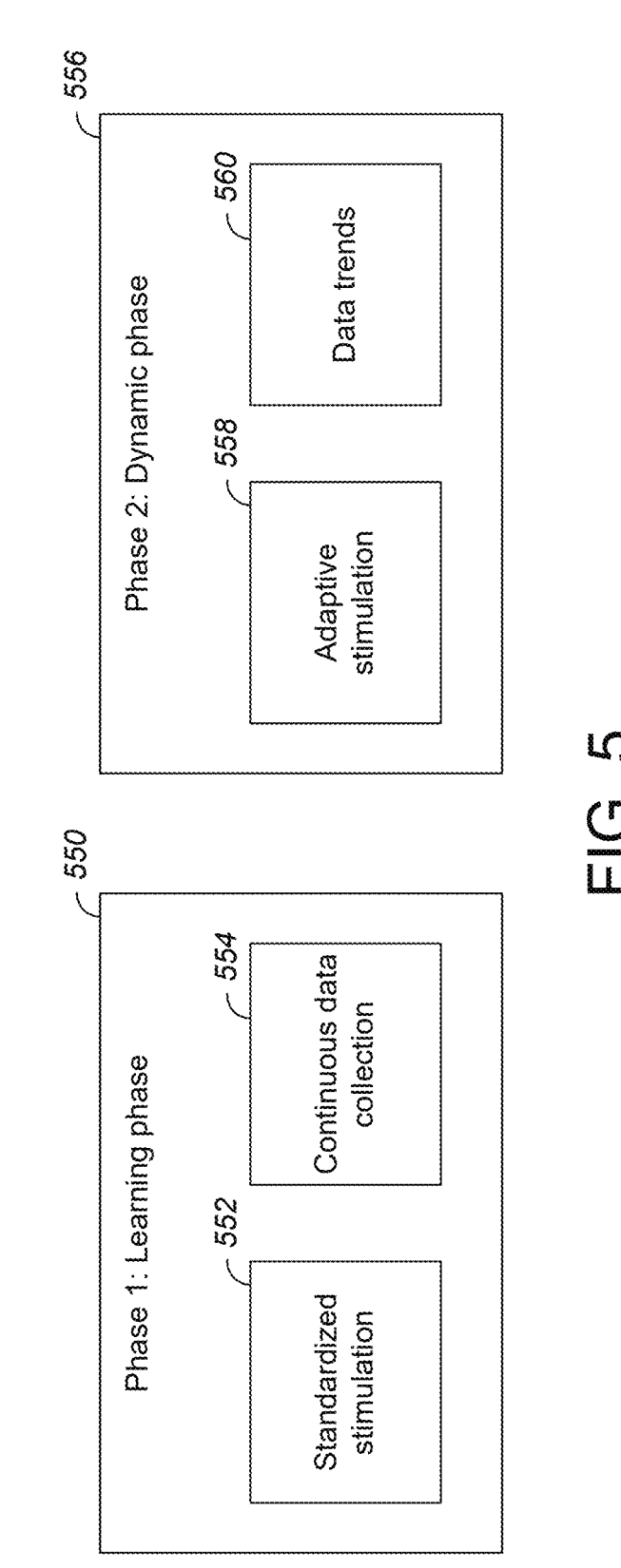
FIG. 5 is a schematic of the adaptive feedback loop, showing the FIG. 5 progression from a learning phase to autonomous stimulation control with real-time adjustment based on physiological deviations, as constructed in accordance with at least one embodiment.

FIG. 5 illustrates an adaptive feedback loop (548), showing the progression from a learning phase to autonomous stimulation control with real-time adjustment based on physiological deviations. In Phase 1 (550), the system operates in a learning phase, during which it delivers standardized or semi-standardized stimulation (552) while collecting continuous physiological and behavioral data (554). This enables the system to establish an individualized treatment profile by capturing baseline autonomic trends, circadian rhythms, and markers of responsiveness. In Phase 2 (556), the system transitions to dynamic adaptive stimulation (558), adjusting output in real time based on the patient's evolving physiological trends (560).

Stimulation Parameters and Adjustment Logic

The closed-loop or partially closed-loop BAT system delivers neuromodulatory therapy by dynamically modulating key electrical stimulation parameters that govern the engagement of baroreceptors. These parameters can include pulse amplitude (intensity of each electrical impulse), frequency (number of pulses per second), pulse width (duration of each pulse), and duty cycle (proportion of time within a stimulation period during which pulses are delivered). Together, these variables determine the magnitude, timing, and temporal pattern of baroreceptor activation, allowing the system to tailor therapy to the patient's physiological needs in real time and optimize modulation of sympathetic and parasympathetic tone.

At system setup, initial stimulation settings and therapy limits can be configured during an in-office visit. Based on baseline physiological metrics, such as resting heart rate, blood pressure, and HRV, as well as real-time patient feedback, the physician and patient can collaboratively define an operating window for therapy. This includes a starting point for stimulation and a maximum allowable therapy threshold that ensures the patient does not experience pain or other adverse effects. This operating window acts as a safety constraint, within which the closed-loop system is permitted to adjust therapy dynamically. As the patient's condition improves, this window may be modified by the care team to accommodate broader therapeutic ranges.

During therapy, the system can continuously monitor physiological inputs and adjust stimulation accordingly. For instance, if an increase in heart rate or physical activity is detected via accelerometers or ECG sensors, the system may elevate frequency or amplitude to counteract sympathetic activation. If inflammatory markers such as TNF-α or IL-6 rise, the system may increase pulse width or duty cycle to suppress systemic inflammation. Conversely, during periods of rest or sleep, the system may reduce stimulation intensity in alignment with circadian rhythms, conserving energy and avoiding overstimulation.

In certain embodiments, the system also constructs and continually refines a patient-specific dose-response model, mapping changes in stimulation parameters to therapeutic outcomes (e.g., blood pressure reduction, improved HRV, decreased inflammatory burden). Referencing this model, the system can determine the minimum effective dose needed to maintain therapeutic benefit, further enhancing tolerability, battery longevity, and long-term stability, while remaining constrained by the predefined therapy window.

Figure 6:
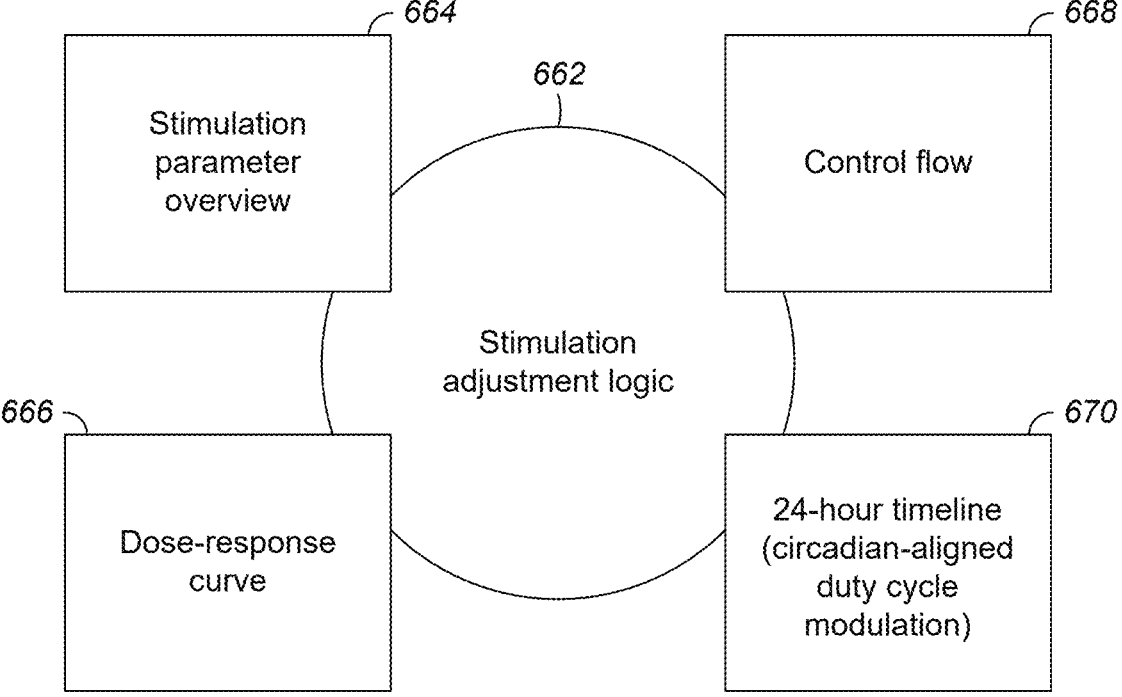
FIG. 6 visualizes the stimulation adjustment logic, including programmable parameter ranges, a dose-response curve, real-time control flow, and circadian-aligned duty cycle modulation, as constructed in accordance with at least one embodiment.

As illustrated in FIG. 6, the closed-loop or partially closed-loop BAT system can utilize a logic architecture to dynamically adjust stimulation parameters in real time. The figure presents a comprehensive schematic concept for stimulation parameters and adjustment logic (662), beginning with a labeled table summarizing key programmable parameters. Each row may correspond to a stimulation variable—amplitude, frequency, pulse width, and duty cycle—with associated programmable ranges (e.g., amplitude: 0.1-10 mA; frequency: 5-100 Hz) and annotations explaining their clinical significance (e.g., "Amplitude: Modulates intensity of baroreceptor activation"). This overview (664) can establish the adjustable framework through which the system tailors neuromodulation to patient-specific needs.

A dose-response curve (666) can graphically represent the relationship between stimulation intensity and therapeutic outcomes. The x-axis may denote stimulation intensity, such as amplitude, while the y-axis may indicate a relevant physiological response, such as reduction in systolic blood pressure. Key inflection points can be labeled, including the minimum effective dose and the saturation point beyond which further increases in stimulation yield no additional benefit. This visualization can support dose optimization, allowing the system to deliver the lowest effective dose necessary to achieve therapeutic goals while minimizing energy use and side effects.

The control flow diagram (668) can further illustrate how physiological data can drive adaptive stimulation. This sequential flowchart can outline the system's real-time feedback process, beginning with sensor input—including HRV, inflammatory cytokine levels, and physical activity data— which is then passed through a signal processing module for noise reduction and trend analysis. The filtered data can be evaluated against a model reference, such as the patient's personalized dose-response profile, to identify meaningful deviations from baseline. The final step, adjustment output, can trigger dynamic modulation of stimulation parameters— amplitude, frequency, pulse width, and/or duty cycle—as needed to maintain therapeutic efficacy.

A 24-hour timeline (670) can visualize how the system modulates stimulation delivery throughout the day. During waking hours, stimulation intensity and duty cycle may be elevated in response to increased sympathetic tone or stress. In contrast, nighttime stimulation is often reduced or paused to promote recovery and conserve battery life, reflecting a circadian-aligned control strategy.

Alternative Embodiments

The BAT system may be implemented in a range of alternative configurations to address diverse clinical scenarios, accommodate patient preferences, and adapt to specific therapeutic needs. This modular and scalable design enables the delivery of personalized autonomic neuromodulation across various care settings and disease contexts.

In one embodiment, the BAT system is configured as a non-invasive device that uses externally placed surface electrodes to deliver transcutaneous electrical stimulation to the underlying carotid sinus. This configuration is particularly suited for patients who are not ideal candidates for surgical implantation, such as pediatric patients, individuals with elevated procedural risk, or those undergoing short-term evaluation to determine responsiveness prior to permanent system placement. A wearable controller, for example, a neckband or adhesive patch, regulates stimulation delivery and offers a reversible, convenient treatment option.

In another embodiment, the system supports bilateral stimulation, utilizing leads positioned at both the left and right carotid sinuses. This configuration enables symmetrical engagement of baroreceptor fields, which may be advantageous in patients with asymmetric baroreceptor sensitivity, severe autonomic dysfunction, or treatment-resistant conditions. Bilateral systems may provide broader and more uniform autonomic modulation, enhancing therapeutic consistency.

The BAT platform may also be integrated with other implanted or wearable medical devices to support coordinated care strategies and enhance therapeutic outcomes. These complementary devices may include implantable cardioverter-defibrillators (ICDs), which detect and treat arrhythmias; insulin pumps, which enable continuous glucose monitoring and insulin delivery for diabetic patients; peripheral artery disease (PAD) monitors that assess vascular perfusion; and gastrointestinal sensors designed to monitor motility or digestive biomarkers in individuals with autonomic gut dysfunction. By enabling seamless communication between the BAT system and these devices, the platform supports cross-system coordination and more comprehensive management of complex, multisystem conditions.

Through secure wireless communication protocols, these devices can exchange real-time data with the BAT system. For example, if an insulin pump detects a hyperglycemic episode, the BAT controller may increase stimulation intensity to help regulate autonomic metabolic response. Likewise, arrhythmic events detected by an ICD may prompt temporary adjustments to BAT parameters to restore autonomic balance.

A cloud-connected data hub enables seamless integration with electronic medical records (EMRs), wearable health trackers, and third-party digital health platforms. This ecosystem allows clinicians to access a comprehensive longitudinal view of patient health, therapy response, and sensor trends. These insights can support early identification of clinical deterioration, inform data-driven therapeutic adjustments, and enable proactive care planning.

To ensure safe and reliable function, the BAT system incorporates multiple fail-safe mechanisms. These include stimulation limiters that cap the maximum allowable intensity and duty cycle, artifact rejection algorithms that filter out corrupted or noisy sensor data, and automatic shutdown protocols that deactivate stimulation in response to predefined fault conditions or safety anomalies. Additionally, the system features fallback operational modes designed to preserve essential functionality in the event of communication loss or component failure, thereby maintaining therapeutic continuity under adverse conditions.

Figure 7:
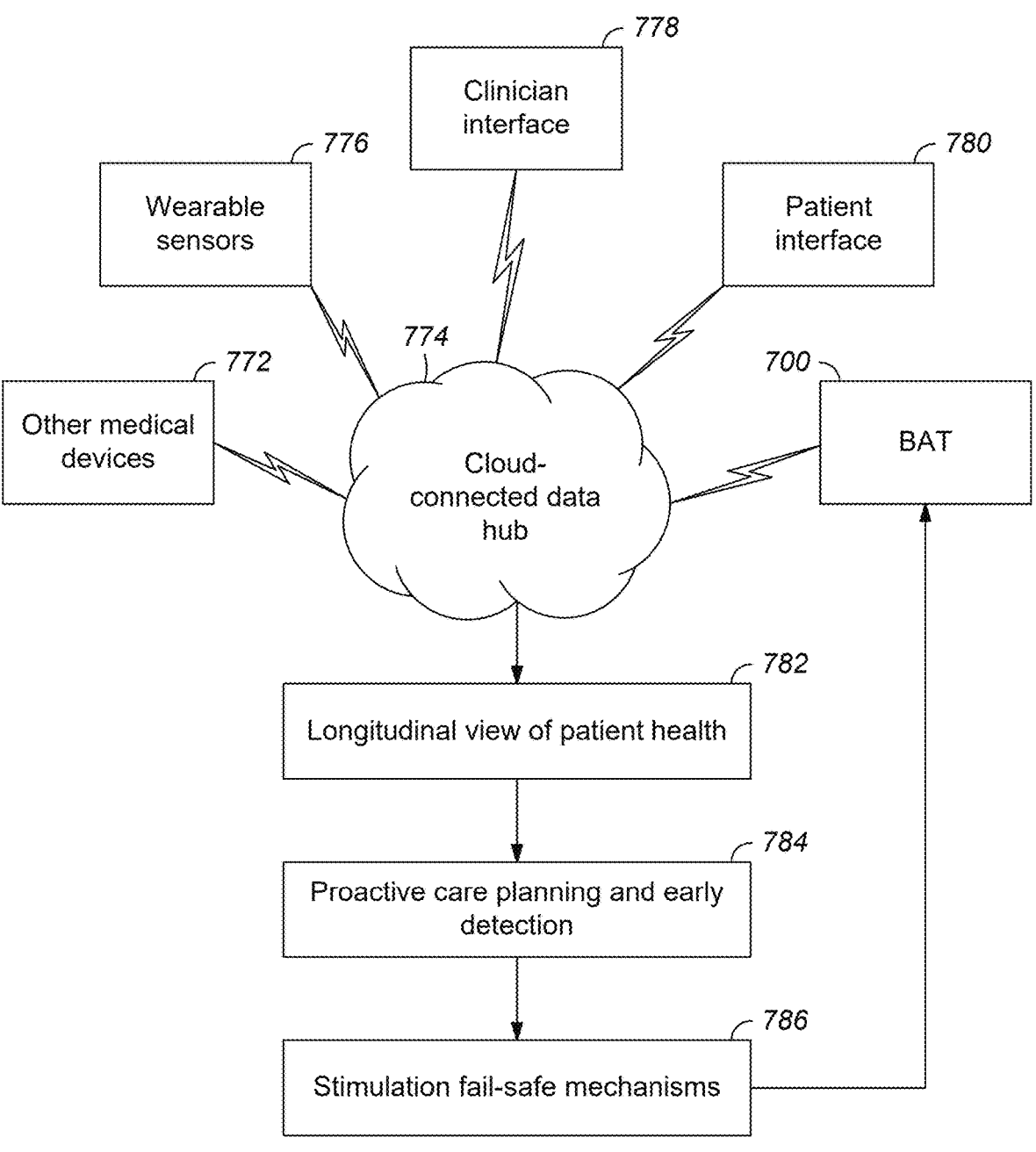
FIG. 7 illustrates integration of the BAT system with other medical devices, a cloud-connected data hub, and safety features, as constructed in accordance with at least one embodiment.

As illustrated in FIG. 7, the BAT system can be designed to operate within a broader therapeutic and digital health ecosystem, supporting both integrated functionality and secure, resilient operation. The schematic concept for alternative embodiments highlights the system's ability to connect with a range of integrated medical devices (772). These can include ICDs for arrhythmia detection and intervention, insulin pumps for continuous glucose monitoring and metabolic regulation, PAD monitors for tracking vascular perfusion, and gastrointestinal sensors for motility assessment and gut biomarker analysis. Arrows show secure wireless communication protocols that facilitate real-time data exchange between these devices and the BAT system (700).

For example, if an ICD detects an arrhythmic event, the BAT system may automatically adjust stimulation to restore autonomic stability; similarly, metabolic fluctuations detected by an insulin pump may inform changes in BAT output to modulate sympathetic influence on glucose metabolism.

Also featured in FIG. 7 is a cloud-connected data hub (774), which can aggregate data from the BAT system (700), wearable health trackers (776), electronic medical records stored in a clinician interface (778), for example, and a patient interface (780). The centralized cloud infrastructure can enable a longitudinal view of patient health (782), supporting trend analysis, and early detection of clinical deterioration and proactive care planning (784). This interoperability enhances clinical decision-making and ensures continuity of care across settings and specialties.

To further safeguard patient safety and system reliability, the diagram includes a safety protocol panel that visualizes multiple fail-safe mechanisms (786) that can be built into the platform. These can include stimulation limiters that cap the maximum allowable amplitude and duty cycle to prevent overstimulation; artifact rejection algorithms that filter out corrupted or noisy physiological signals; and automatic shutdown protocols that deactivate stimulation in response to predefined fault conditions or anomalies. The system can also include fallback operational modes that preserve essential functionality, such as basic rhythmic stimulation, in the event of wireless communication loss or hardware failure, thereby ensuring continuous therapy delivery even under adverse conditions.

Together, these visual elements underscore the flexibility, connectivity, and robust safety architecture of the BAT platform, reinforcing its suitability for personalized autonomic neuromodulation across a diverse range of cardiovascular, metabolic, inflammatory, and neuroimmune disorders.

External Programmer and Clinician Interface

The BAT system can include a secure, cloud-connected clinician dashboard that allows healthcare providers to remotely monitor, manage, and optimize patient therapy. Accessible via desktop, tablet, or other authorized devices, this clinician-facing interface provides both real-time and historical insights, enabling longitudinal tracking of therapy outcomes, remote parameter adjustment, and early identification of clinical trends that may warrant intervention.

The dashboard can present a comprehensive view of the patient's physiological status based on multimodal sensor data. Monitored metrics may include HRV, blood pressure, bioimpedance, activity level, and inflammatory biomarkers such as TNF-$\alpha$ and IL-6. Interactive visualizations allow clinicians to correlate physiological trends with stimulation activity, assess therapy effectiveness, and determine whether adjustment of stimulation parameters is needed.

Stimulation settings, including pulse amplitude, frequency, pulse width, and/or duty cycle, can be reviewed and modified directly through the dashboard. These adjustments may be made in response to sensor-derived physiological data or patient-reported symptoms received via the mobile application. For example, if a patient reports fatigue or dizziness, a clinician may lower pulse amplitude or reduce duty cycle. Conversely, if biomarker levels suggest systemic inflammation, duty cycle or frequency may be increased accordingly.

To support proactive care, the system may incorporate automated alerts triggered by significant deviations from established baselines. For instance, if the system detects a sustained drop in HRV or a sharp increase in blood pressure, it issues a notification categorized by severity and urgency.

Example alerts may include: "BP exceeds threshold—review recommended within 24 hours" and "Cytokine levels elevated—consider increasing duty cycle."

To enhance decision support, the dashboard can also include an AI-powered recommendation engine. This system analyzes both real-time and historical data to identify patterns and generate data-driven suggestions. Recommendations may be personalized based on the patient's individual trends or drawn from population-level benchmarks. For instance, the dashboard may suggest: "Increase frequency to counteract sympathetic activity," or "Reduce amplitude by 10% to mitigate overstimulation." These insights can be presented in a dedicated "Recommendation" panel for clinician review and approval.

The clinician interface is designed to reduce the need for in-person reprogramming, facilitate efficient therapy titration, and improve continuity of care. It offers centralized access to aggregated patient data, facilitates longitudinal tracking, and allows providers to tailor therapy as the patient's clinical condition evolves.

Figure 8:
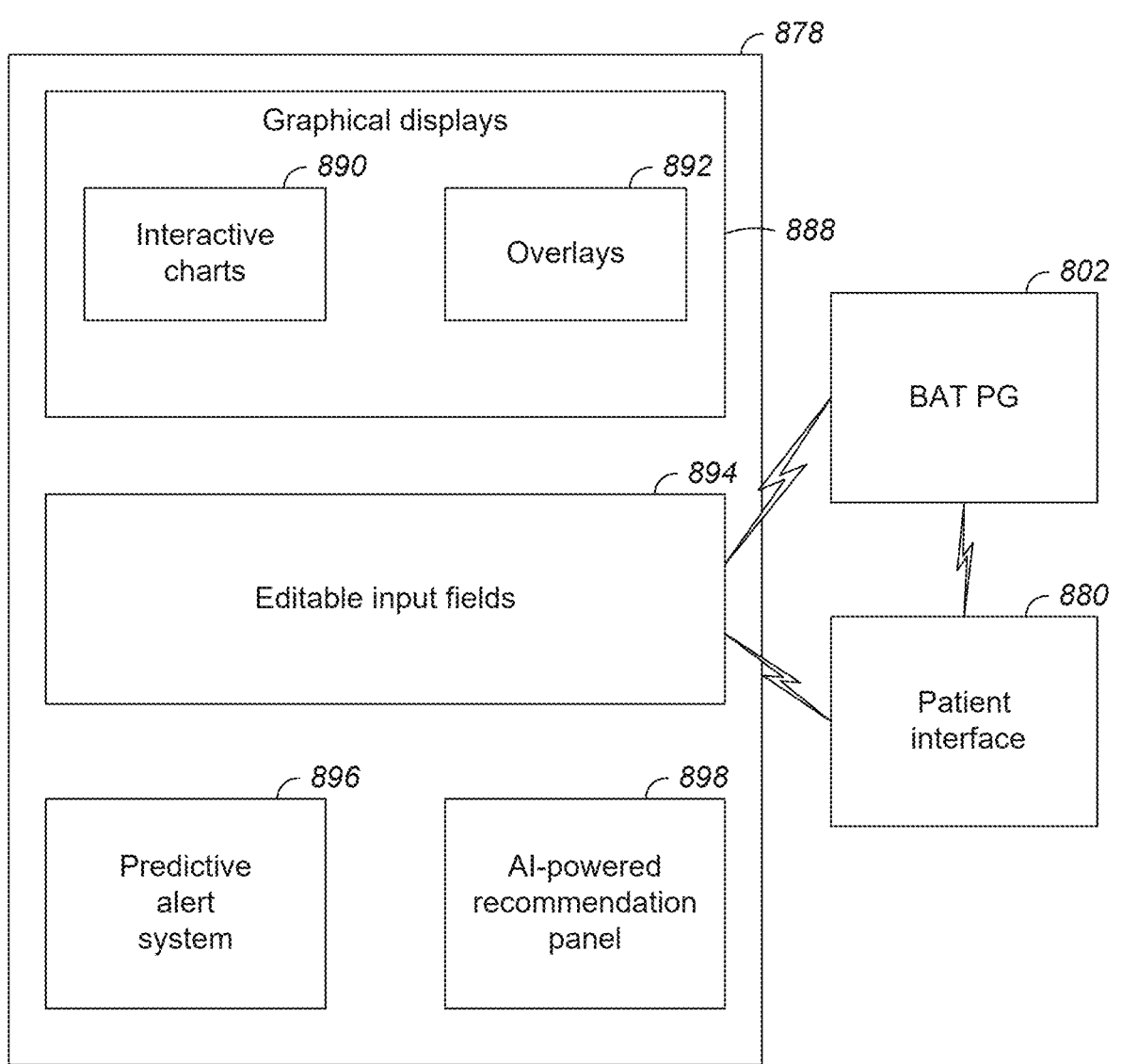
FIG. 8 is a mock-up of the clinician dashboard, displaying patient trends, editable therapy settings, predictive alerts, AI-generated recommendations, and a secure data flow between system components, as constructed in accordance with at least one embodiment.

As illustrated in FIG. 8, the BAT system includes a clinician-facing external programmer in the form of a secure, cloud-connected dashboard (878) designed to support personalized therapy management. The clinician dashboard mock-up features a series of graphical displays (888), including interactive charts (890) that show trends in monitored physiological metrics over time. These may include HRV, blood pressure, and inflammatory biomarkers such as TNF-α and IL-6, plotted alongside corresponding stimulation settings. Overlays (892) can allow clinicians to correlate specific physiological changes with prior adjustments in therapy, providing valuable insights into treatment efficacy and trends. Adjacent to these visualizations are editable input fields (894) displaying current stimulation parameters, such as pulse amplitude, frequency, and duty cycle, which can be modified using drop-down menus or sliders, enabling remote and precise customization of therapy settings.

To further support proactive care, FIG. 8 includes a predictive alert system (896) that can feature banner alerts that are triggered when monitored data deviate significantly from established baselines. Severity can be visually categorized, for example, red for critical issues and yellow for moderate deviations, with sample alerts such as "BP exceeds threshold—review recommended within 24 hours" and "Elevated cytokine levels—consider increasing stimulation frequency." These alerts can be annotated to emphasize their role in enabling early clinical intervention and maintaining therapeutic safety. A dedicated AI-powered recommendation panel (898) can present real-time suggestions based on both individual and population-level trends. These insights may include recommendations such as "Increase frequency to 40 Hz" or "Reduce amplitude by 10% to mitigate overstimulation," and are displayed with options for clinician review and approval before implementation.

Finally, the cloud-connected data flow diagram included in FIG. 8 illustrates bidirectional communication between the implanted BAT device (or wearable stimulator) (802), the patient's mobile application (880), and the clinician dashboard (878). The mobile app enables patients to submit self-reported symptoms and receive notifications, while the cloud infrastructure facilitates secure, seamless data exchange and centralized access for providers. Together, these elements underscore the BAT system's ability to deliver adaptive, responsive therapy while streamlining clinician oversight and enhancing continuity of care across diverse settings.

Patient User Interface

The BAT system can include a dedicated mobile application designed to enhance patient engagement, facilitate therapy adherence, and enable two-way interaction between the patient and the broader BAT platform. This patient-facing interface can serve as a central hub for real-time health monitoring, symptom reporting, and wellness support, empowering individuals to play an active role in their treatment.

The application may display intuitive, visual representations of longitudinal health trends, including HRV, blood pressure, physical activity, and, in some embodiments, inflammatory biomarker levels such as TNF-α and IL-6. Patients can track how these physiological markers evolve over time, gaining insight into their current status and the effects of neuromodulatory therapy. Information can be presented via interactive graphs, summary tiles, and alerts, all designed for ease of interpretation and accessibility.

In addition to objective health data, the mobile interface can enable patients to submit subjective feedback regarding symptoms or overall well-being. Input methods may include sliders, checkboxes, surveys, or voice prompts, capturing information on fatigue, dizziness, anxiety, stress, pain, and other relevant sensations. This patient-reported data can be integrated into the closed-loop or partially closed-loop system, enhancing personalization of therapy by supplementing physiological sensor inputs with real-world, patient-perceived outcomes.

The application can also include a range of features to support daily health management and device usage. These features may include reminders for medication schedules, therapy adherence, and upcoming clinical appointments, as well as notifications related to battery status, device maintenance, and potential communication issues. An integrated education center can provide curated videos, frequently asked questions, interactive guides, and behavior coaching tools designed to improve patient understanding of BAT and its clinical objectives.

The system may be further enhanced through seamless integration with wearable devices such as smartwatches, hydration patches, biosensing garments, and fitness trackers. These peripherals continuously monitor important health metrics, including heart rate, step count, sleep quality and duration, hydration levels, and overall movement patterns. In certain embodiments, changes detected by these devices, such as increased physical exertion or elevated stress, can trigger automatic adjustments to stimulation parameters. This creates a semi-autonomous feedback loop in which therapy dynamically adapts to real-world behavior and environmental context.

Figure 9:
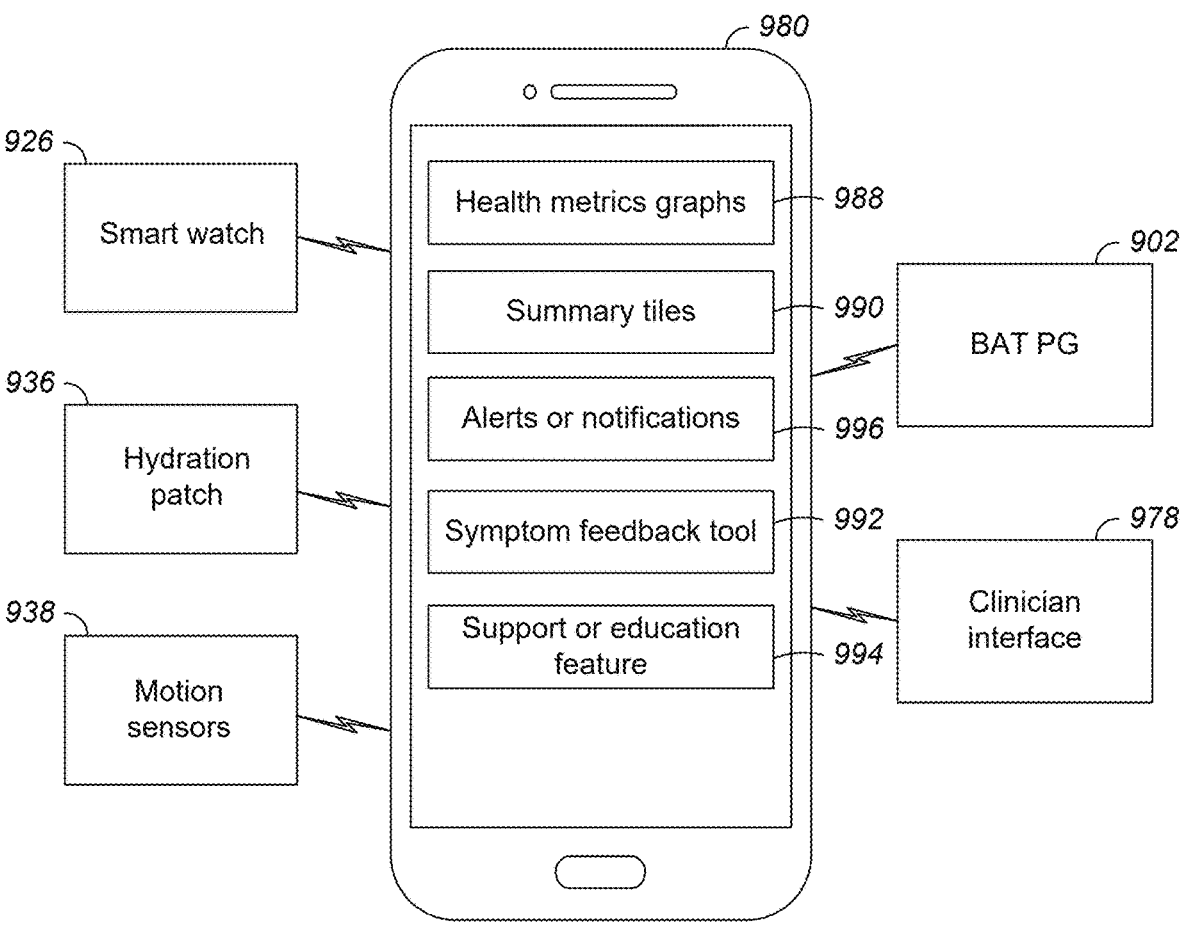
FIG. 9 is a mock-up of the patient mobile application interface, including health tracking dashboards, symptom input tools, wearable sensor connectivity, and supportive features for engagement and education, as constructed in accordance with at least one embodiment.

As illustrated in FIG. 9, the BAT system includes a patient user interface (980) in the form of a mobile application designed to promote engagement, therapy adherence, and real-time interaction with the BAT ecosystem. The patient dashboard is displayed on a smartphone screen and includes interactive graphs (988) showing longitudinal trends in key health metrics such as HRV, blood pressure, physical activity, and, in some embodiments, inflammatory biomarkers like TNF-α and IL-6. Alongside these charts, summary tiles (990) provide quick visual overviews of daily or weekly averages, and alerts or notifications (996) may appear, such as "Cytokine levels elevated—stay hydrated," to encourage proactive health behaviors and reinforce treatment goals.

An intuitive symptom feedback tool (992) invites patients to report how they're feeling each day. This may take the form of a slider labeled "How are you feeling today?" with adjustable input fields for symptoms like fatigue, pain, stress, dizziness, and anxiety. For greater accessibility, users may also enter data through voice prompts or touch-based controls. The application supports therapy management through reminders and notifications related to medications, therapy schedules, and device maintenance, helping patients stay on track with minimal effort. A built-in education center (994) can provide curated videos, FAQs, and interactive guides explaining the purpose and benefits of BAT, along with behavior coaching tips such as hydration and activity goals. The app can also deliver motivational messages—like "Your therapy is on track!"—to foster adherence and patient confidence.

FIG. 9 also illustrates wearable device integration, highlighting real-time connections between the mobile app and peripherals such as smartwatches (926) for heart rate and step count, hydration patches (936) for fluid monitoring, and motion sensors (938) to track sleep and activity cycles. A connectivity diagram visualizes how these wearables and the clinician interface (978) feed data into the BAT PG (902), creating a synchronized, patient-centered feedback loop. Together, these features support a dynamic and individualized approach to neuromodulation, one that empowers patients to play an active role in managing chronic conditions rooted in autonomic dysfunction.

Conclusion

Existing BAT systems rely on open-loop or manually programmed stimulation protocols, delivering fixed outputs that fail to adapt to the dynamic and individualized nature of autonomic dysfunction. Such systems may overlook real-time physiological changes related to heart rate variability, inflammatory status, physical activity, or circadian influences, for example, limiting their therapeutic precision and placing additional demands on clinical oversight.

The present disclosure addresses these limitations by introducing a platform for delivering BAT through closed-loop or partially closed-loop systems. The disclosed systems and methods can integrate multimodal sensor data, real-time analytics, and beat-to-beat modulation capabilities to personalize therapy delivery. Stimulation parameters such as pulse amplitude, frequency, and duty cycle can be dynamically adjusted in response to physiological signals and patient-reported inputs.

With AI-powered algorithms, clinician dashboards, patient interfaces, and compatibility with wearable or implantable technologies, the platform enables proactive, responsive, and scalable neuromodulation. This intelligent architecture enhances treatment for a wide range of cardiovascular, inflammatory, metabolic, and pain-related conditions by providing personalized, data-driven therapy designed to optimize outcomes and support long-term disease management.

The above Detailed Description includes references to the accompanying drawings, which form a part of the Detailed Description. The Detailed Description should be read with reference to the drawings. The drawings show, by way of illustration, specific embodiments in which the present systems and methods can be practiced. These embodiments are also referred to herein as "examples."

The above Detailed Description is intended to be illustrative and not restrictive. For example, the above-described examples (or one or more features or components thereof) can be used in combination with each other. Other embodiments can be used, such as by one of ordinary skill in the art upon reviewing the above Detailed Description. Also, various features or components have been or can be grouped together to streamline the disclosure. This should not be interpreted as intending that an unclaimed disclosed feature is essential to any claim. Rather, inventive subject matter can lie in less than all features of a particular disclosed embodiment. Thus, the following claim examples are hereby incorporated into the Detailed Description, with each example standing on its own as a separate embodiment:

In Example 1, a method for treating a condition associated with autonomic dysfunction in a patient comprises delivering electrical stimulation to one or more baroreceptors via a pulse generator; collecting physiological data from at least one sensor configured to monitor one or more of ECG, heart rate, heart rhythm, heart rate variability, blood pressure, bioimpedance, inflammatory cytokine levels, EMG, acoustics, and physical activity levels; analyzing the collected data to assess autonomic nervous system activity; and dynamically adjusting one or more stimulation parameters based on the analysis to modulate sympathetic and parasympathetic tone.

In Example 2, the method of Example 1 is optionally configured such that electrical stimulation is adjusted on a beat-to-beat basis using ECG data as input. In Example 3, the method of Example 1 is optionally configured such that the duty cycle of stimulation is dynamically adjusted based on time of day or patient activity level.

In Example 4, the method of any one of Examples 1-3 is optionally configured such that physiological data is collected from at least two of: wearable sensors, implantable sensors, and external sensors.

In Example 5, the method of any one of Examples 1-4 optionally further comprises applying one or more artificial intelligence algorithms to predict patient-specific responses and guide adjustments of the stimulation parameters.

In Example 6, the method of any one of Examples 1-5 is optionally configured such that ECG waveform data is correlated with acoustic signals or physical activity levels to identify early signs of heart failure decompensation.

In Example 7, the method of any one of Examples 1-6 optionally further comprises using ECG data to evaluate therapeutic effectiveness and guide adjustment of stimulation parameters.

In Example 8, the method of any one of Examples 1-7 is optionally configured such that continuous ECG waveform data is analyzed using one or more artificial intelligence algorithms to assess patient status and inform stimulation adjustments.

In Example 9, the method of any one of Examples 1-8 optionally further comprises integrating patient-reported symptoms via a patient interface to influence stimulation adjustments.

In Example 10, the method of Example 9 is optionally configured such that the patient interface comprises selectable feedback elements configured to maintain, increase, or decrease stimulation intensity or frequency.

In Example 11, the method of any one of Examples 1-10 optionally further comprises wirelessly transmitting physiological data to a clinician dashboard configured for remote monitoring and adjustment of stimulation parameters.

In Example 12, the method of any one of Examples 1-11 is optionally configured such that electrical stimulation is delivered via a multi-channel lead targeting multiple baroreceptor regions.

In Example 13, the method of any one of Examples 1-12 optionally further comprises adjusting stimulation frequency in coordination with the patient's cardiac cycle.

In Example 14, the method of any one of Examples 1-13 is optionally configured such that the electrical stimulation is delivered non-invasively during acute inflammatory episodes.

In Example 15, the method of any one of Examples 1-13 is optionally configured such that the pulse generator is implantable, wirelessly powered, and configured to receive stimulation instructions remotely.

In Example 16, the method of any one of Examples 1-15 is optionally configured such that stimulation parameters are adjusted based on combined inputs from heart rate variability, bioimpedance, and physical activity levels.

In Example 17, a system for treating a condition associated with autonomic dysfunction in a patient comprises a pulse generator configured to deliver electrical stimulation to one or more baroreceptors; a sensor suite configured to collect physiological data; a controller configured to analyze the collected data and adjust stimulation parameters; and a patient engagement platform.

In Example 18, the system of Example 17 is optionally configured such that the controller is a closed-loop feedback controller that autonomously adjusts stimulation parameters in response to changes in physiological data.

In Example 19, the system of any one of Examples 17 or 18 is optionally configured such that the physiological data includes ECG data, and the controller adjusts stimulation on a beat-to-beat basis using ECG input.

In Example 20, the system of any one of Examples 17-19 is optionally configured such that the controller correlates ECG variability data with accelerometer-based activity and acoustic data to detect early signs of heart failure decompensation.

In Example 21, the system of any one of Examples 17-20 is optionally configured such that the controller includes artificial intelligence algorithms to analyze continuous ECG waveform data and guide stimulation adjustments.

In Example 22, the system of any one of Examples 17-21 is optionally configured such that the patient engagement platform includes a user interface for patient-reported symptoms, which are used to adjust stimulation intensity or frequency.

In Example 23, the system of Example 22 is optionally configured such that the patient engagement platform comprises one or more wearable devices configured to monitor patient biometrics.

In Example 24, the system of any one of Examples 17-23 is optionally configured such that the sensor suite comprises an accelerometer configured for acoustic monitoring of physiological sounds indicative of autonomic or cardiopulmonary status.

Definitions and Interpretations

Throughout this patent document, specific terms are used to refer to particular features, components, and method steps. As one skilled in the art will recognize, different terminology may be used to describe the same or similar elements. The terminology used herein is not intended to limit the scope of the invention to any particular nomenclature. Instead, the terms should be understood in accordance with their function within the systems and methods described.

Unless explicitly defined otherwise within this document, the following definitions shall apply. The terms "a," "an," and "the" refer to one or more than one, irrespective of whether the phrase "at least one" or "one or more" is used in other contexts. The term "or" should be interpreted as a nonexclusive disjunction, meaning that "A or B" includes (i) A but not B, (ii) B but not A, and (iii) both A and B.

All numerical values provided in this disclosure should be understood as approximate values, whether explicitly stated or not, and are assumed to be modified by the term "about." The term "about" encompasses numerical variations that are considered functionally equivalent by those skilled in the art. This may include rounding to the nearest significant figure or values within an equivalent range. Additionally, when numerical ranges are provided, the endpoints are inclusive of all intermediate values and subranges. For example, the range 1 to 4 includes 1, 1.5, 1.75, 2, 2.3, 2.6, 2.9, etc., as well as subranges such as 1 to 1.5, 1 to 2, 1 to 3, 2 to 3.5, 2 to 4, 3 to 4, etc.

Scope and Claim Construction

The scope of the present systems and methods should be determined with reference to the appended claims, along with the full scope of equivalents to which such claims are entitled. In the claims, the term "including" is to be interpreted as the plain-English equivalents of "comprising" and "wherein." The use of "including" and "comprising" in a claim should be understood as open-ended terminology, meaning that a system or method that includes additional features or components beyond those listed still falls within the scope of the claim.

ABSTRACT INTERPRETATION

The Abstract of this application is provided solely for the purpose of enabling a quick understanding of the technical disclosure. It is submitted with the express understanding that it will not be used to interpret or limit the scope or meaning of the claims. The present systems and methods should be construed based on the full scope of the Detailed Description and claims, rather than any limitations inferred from the Abstract.

What is claimed:

1. A method of delivering baroreflex activation therapy to a patient in a closed-loop or partially closed-loop configuration, the method comprising:

delivering electrical stimulation to a baroreceptor region with a pulse generator;

collecting physiological data from at least one sensor configured to monitor one or more of electrocardiography (ECG), rate variability (HRV), blood pressure, bioimpedance, acoustics, electromyography (EMG), and physical activity;

analyzing the collected physiological data to assess autonomic nervous system activity; and adjusting at least one stimulation parameter or stimulation timing in response to the analysis to modulate baroreflex activity, wherein the adjusting occurs on a beat-to-beat basis using timing information derived from ECG input such that delivery of the electrical stimulation is synchronized to successive cardiac cycles, and wherein the beat-to-beat adjusting is performed independently of longer-term duty-cycle scheduling, circadian modulation, or time-of-day-based therapy programming.

2. The method of claim 1, wherein the adjusted stimulation parameter comprises a duty cycle that is dynamically modulated based on time of day or detected patient activity.

3. The method of claim 1, wherein the physiological data are fused from at least two sensors selected from wearable sensors, implantable sensors, and external sensors.

4. The method of claim 1, further comprising applying artificial intelligence or machine-learning algorithms trained on real-time data, historical data, or both, to guide the adjusting.

5. The method of claim 1, wherein ECG-derived HRV is correlated with accelerometer-derived activity data or acoustic signals to detect early signs of heart-failure decompensation and to preemptively modify stimulation.

6. The method of claim 1, further comprising receiving patient-reported inputs via a patient application and using the inputs to maintain, increase, or decrease stimulation intensity or frequency.

7. The method of claim 1, further comprising wirelessly transmitting physiological data and therapy data to a clinician dashboard for remote review and optional parameter updates.

8. The method of claim 1, further comprising establishing a patient-specific physiological baseline, and preemptively adjusting the stimulation parameters when one or more monitored physiological signals deviate from the baseline by a threshold amount indicative of impending autonomic imbalance.

9. The method of claim 1, further comprising dynamically weighting or disregarding one or more physiological inputs based on signal quality metrics before adjusting the stimulation parameters.

10. A method of delivering baroreflex activation therapy to a patient in a closed-loop or partially closed-loop configuration, the method comprising:

delivering electrical stimulation to a baroreceptor region with a pulse generator;

collecting physiological data from at least one sensor configured to monitor one or more of electrocardiography (ECG), rate variability (HRV), blood pressure, bioimpedance, acoustics, electromyography (EMG), and physical activity;

analyzing the collected data to assess autonomic nervous system activity; and adjusting at least one stimulation parameter in response to the analysis to modulate baroreflex activity, wherein the adjusting occurs on a beat-to-beat basis using ECG input, and wherein the adjusted stimulation parameter comprises a duty cycle that is dynamically modulated based on time of day or detected patient activity.

11. A baroreflex activation therapy system configured for closed-loop or partially closed-loop operation, comprising:

a pulse generator configured to deliver electrical stimulation to one or more baroreceptors;

a sensor suite configured to collect physiological data including at least electrocardiography heart rate variability (HRV); and a controller programmed to analyze the collected physiological data and adjust two or more stimulation parameters in response, wherein the controller autonomously adjusts stimulation on a beat-to-beat basis using ECG input such that stimulation is synchronized to the cardiac cycle based on timing information derived from ECG, and wherein the beat-to-beat adjusting is performed independently of longer-term duty-cycle scheduling or circadian therapy programming.

12. The system of claim 11, wherein the controller implements artificial intelligence or machine-learning algorithms that classify autonomic state from continuous or intermittent data and issue parameter recommendations or autonomous parameter updates.

13. The system of claim 11, wherein the pulse generator is implantable and is configured to deliver stimulation to a carotid sinus baroreceptor region.

14. The system of claim 11, further comprising a clinician dashboard that displays longitudinal trends of one or more of HRV, blood pressure, bioimpedance, and activity overlaid with stimulation settings and provides alerts upon threshold deviations.

15. The system of claim 11, further comprising fail-safe controls including one or more of artifact rejection, stimulation limiters, automatic shutdown on fault, and fallback modes.

16. The system of claim 11, wherein the system is configured for bilateral stimulation or sensing with coordinated parameter control between sides.

17. The system of claim 11, wherein the controller performs impedance checks and uses impedance results to adjust contact quality assessment or stimulation safety limits.

18. The system of claim 11, further comprising a communication interface configured to wirelessly transmit therapy and physiological data and to receive configuration updates.

19. The system of claim 11, wherein the controller includes a duty-cycle scheduler configured to vary one or more stimulation characteristics based on circadian patterns or detected activity level.

20. The system of claim 11, wherein the controller implements a hierarchical control scheme in which beat-to-beat ECG-synchronous stimulation control has priority over longer-term duty-cycle or circadian scheduling such that scheduled stimulation parameters are overridden in response to real-time physiological conditions.

* * * * *